United States Patent [19]
Martell et al.

[11] Patent Number: 5,897,836
[45] Date of Patent: *Apr. 27, 1999

[54] THERMAL GAS SENSING APPARATUS

[75] Inventors: Dennis Martell, Naperville; Jan Krcma, Elk Grove Village, both of Ill.

[73] Assignees: J and N Associates, Inc.; Nicor Technologies, Inc.

[*] Notice: This patent issued on a continued prosecution application filed under 37 CFR 1.53(d), and is subject to the twenty year patent term provisions of 35 U.S.C. 154(a)(2).

[21] Appl. No.: 08/770,133

[22] Filed: Dec. 19, 1996

[51] Int. Cl.$^6$ ................................. G01N 27/04
[52] U.S. Cl. ................. 422/90; 422/94; 422/98; 73/25.01
[58] Field of Search ................. 422/90, 91, 94, 422/98; 73/25.01, 25.03

[56] References Cited

U.S. PATENT DOCUMENTS

| | | | |
|---|---|---|---|
| 2,817,229 | 12/1957 | Beard | 73/26 |
| 4,057,755 | 11/1977 | Piesche | 324/62 |
| 4,277,439 | 7/1981 | Yasuda et al. | 422/94 |
| 4,541,988 | 9/1985 | Tozier et al. | 422/94 |
| 4,594,879 | 6/1986 | Maeda et al. | 73/27 R |
| 5,217,692 | 6/1993 | Rump et al. | 422/98 |
| 5,379,630 | 1/1995 | Lacey | 73/25.03 |
| 5,418,131 | 5/1995 | Butts | 422/98 |
| 5,526,280 | 6/1996 | Consadori et al. | 422/95 |
| 5,535,614 | 7/1996 | Okamoto et al. | 73/23.31 |

*Primary Examiner*—Lyle A. Alexander
*Attorney, Agent, or Firm*—Marshall, O'Toole, Gerstein, Murray & Borun

[57] ABSTRACT

A thermal gas sensing apparatus for a gas detector is provided with a gas compartment containing a gas, a gas sensor exposed to the gas in the gas compartment, and a temperature sensor exposed to the gas in the gas compartment. The gas sensing apparatus includes a circuit for generating a gas signal having a magnitude which relates to the heat capacity of the gas and a circuit for generating a temperature signal having a magnitude which relates to the temperature of the gas. The apparatus includes a circuit for supplying a variable magnitude of electrical current through the gas sensor to cause the resistance of the gas sensor to remain substantially constant. The apparatus also includes a difference amplifier for generating a gas concentration signal based upon the temperature signal and the gas signal.

17 Claims, 1 Drawing Sheet

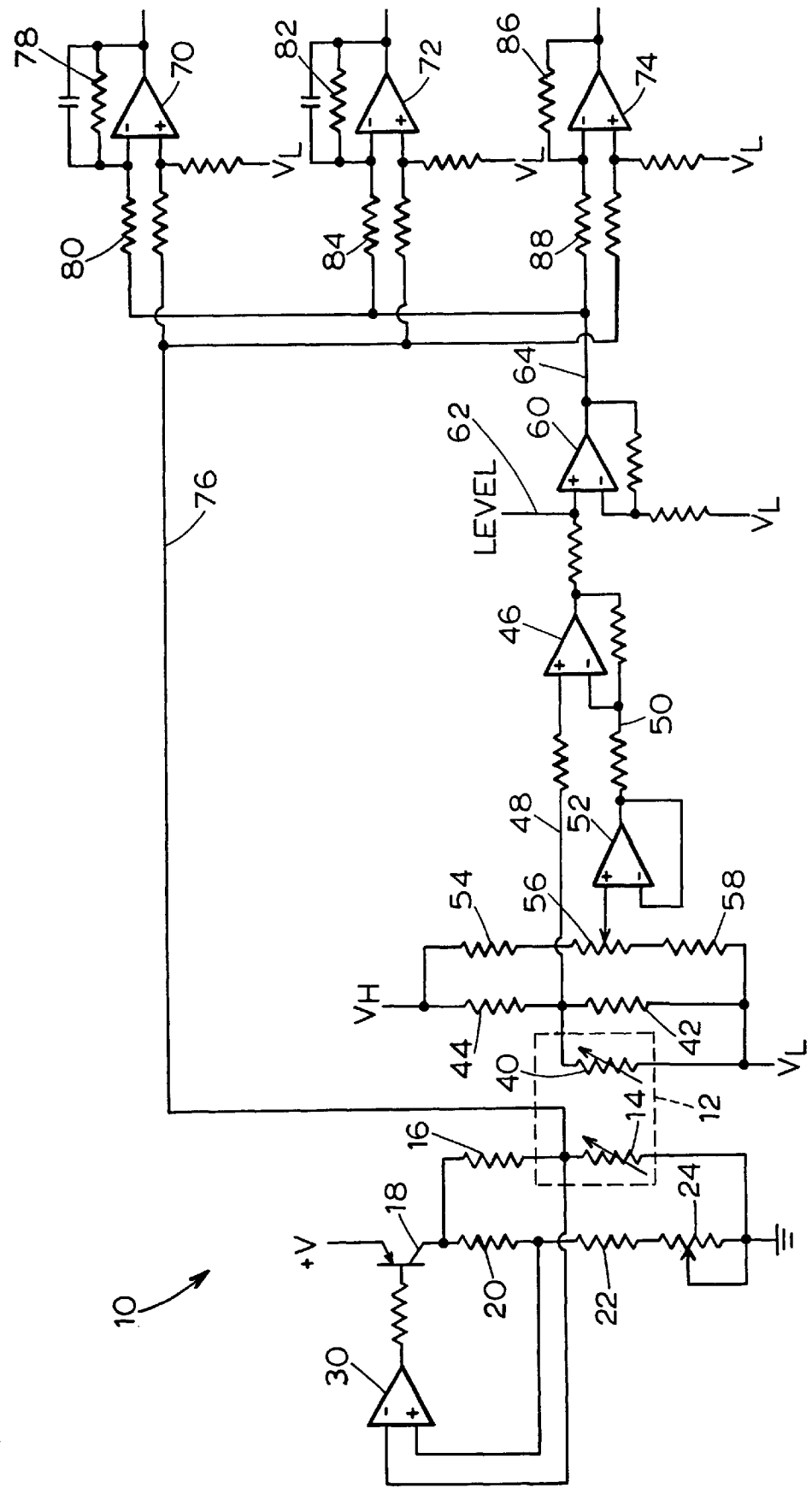

THERMAL GAS SENSING APPARATUS

BACKGROUND OF THE INVENTION

The present invention relates to a thermal gas sensing apparatus for use in a gas detector.

Gas detectors for sensing the concentration of gases are well known. Such gas detectors may be of various types, including catalytic gas detectors and thermal gas detectors. A catalytic gas detector utilizes a gas sensing circuit having a gas sensing element which detects gas based on combustion of the gas, which heats the gas sensing element. One example of a catalytic gas detector is disclosed in U.S. Pat. No. 4,541,988 to Tozier, et al. In that patent, the gas sensing element is coated with a material that acts as a catalyst to promote combustion of the gas being sensed.

Thermal gas detectors operate based on a different principle. A thermal gas detector utilizes a sensing element, such as a thermistor, through which an electrical current is provided and which generates heat within the sensing element. That heat is dissipated at a rate which depends on the particular gas to which the sensing element is exposed. Since different gases have different heat capacities (i.e. the rate at which the gas can absorb heat from the sensing element), a particular gas can be identified by the rate at which the sensing element is cooled.

Conventional thermal gas detectors are typically provided with a gas sensing circuit composed of a current source that supplies a constant electrical current through a pair of sensing elements, which include a reference element which is isolated from the gas being sensed and a sensing element which is exposed to the gas being sensed. The need to isolate the reference element from the gas increases the complexity of the gas sensing circuit and its cost.

SUMMARY OF THE INVENTION

The present invention is directed to a thermal gas sensing apparatus having a gas compartment containing a gas, a gas sensor exposed to the gas, and a temperature sensor exposed to the gas. Since both the gas and temperature sensors are exposed to the gas in the gas compartment, the need to shield one of the sensors from exposure to the gas is eliminated. The gas sensing apparatus includes means for generating a gas signal having a magnitude which relates to the heat capacity of the gas and means for generating a temperature signal having a magnitude which relates to the temperature within the gas compartment. The apparatus includes means for supplying a variable magnitude of electrical current through the gas sensor to cause the resistance of the gas sensor to remain substantially constant. The apparatus also includes means for generating a gas concentration signal based upon the temperature signal and the gas signal.

The apparatus may have means for causing an electrical current to flow through the temperature sensor which has a magnitude that is substantially independent of the magnitude of the electrical current flowing through the gas sensor. The means for generating the gas concentration signal may comprise means for determining the difference between the gas signal and the temperature signal. The means for supplying electrical current through the gas sensor may include a current source and control means for controlling the magnitude of the current based upon the resistance of the gas sensor.

The control means may be an amplifier having a first input connected to sense a voltage across the gas sensor, a second input connected to sense a voltage across a fixed resistance, and an output connected to control the current source. The means for generating the temperature signal may include means for generating an adjustable voltage and means for determining the difference between the adjustable voltage and the voltage across the temperature sensor.

These and other features of the present invention will be apparent to those of ordinary skill in the art in view of the detailed description of the preferred embodiment, which is made with reference to the drawing, a brief description of which is provided below.

BRIEF DESCRIPTION OF THE DRAWING

The FIGURE illustrates a preferred embodiment of a thermal gas sensing apparatus.

DETAILED DESCRIPTION OF A PREFERRED EMBODIMENT

A preferred embodiment of a thermal gas sensing apparatus is illustrated in the figure. As defined herein, a "thermal gas sensing apparatus" is one that utilizes a gas sensor through which an electrical current is provided and in which a particular gas is sensed based upon the heat capacity of the gas, or the rate at which the gas absorbs heat from the gas sensor. Referring to the FIGURE, the gas sensing apparatus 10 has a gas compartment schematically shown at 12 which contains a gas having a particular heat capacity. The gas compartment 12 has at least one aperture or opening (not shown) to facilitate entry of gas therein. A gas sensor 14 (which may be a negative temperature coefficient (NTC) thermistor) is disposed within the gas compartment 12 and exposed to the gas therein.

The gas sensor 14 is connected in series with a resistor 16, which is connected to an electrical current source in the form of a transistor 18. A pair of resistors 20, 22 and a potentiometer 24 are connected in parallel with the resistor 16 and the gas sensor 14. The amount of current provided by the transistor 18 is controlled by an amplifier 30 having a first input which is connected to the junction of the resistor 16 and the gas sensor 14 to sense the voltage across the gas sensor 14 and a second input which is connected to the junction of the resistors 20, 22 to sense the voltage across the resistor 22 and the potentiometer 24.

The control amplifier 30 adjusts the amount of current provided by the transistor 18 so that the resistance of the gas sensor 14 remains substantially constant, regardless of the concentration of gas present in the gas compartment 12. The combined resistance of the resistor 16 and the gas sensor 14 are much smaller (e.g. 100 times smaller) than the combined resistance of the resistors 20, 22 and the potentiometer 24. Consequently, almost all of the current generated by the transistor 18 will pass through the resistor 16 and the gas sensor 14 (and not through the resistors 20, 22 and the potentiometer).

The amplifier 30 acts to hold the voltages on its two inputs substantially equal. Thus, if the temperature of the gas sensor 14 temporarily decreases in response to the presence of a particular gas, its resistance will temporarily increase, and the voltage across the gas sensor 14 will be temporarily greater than the voltage across the resistor 22 and the potentiometer 24. In response to that voltage imbalance, the control amplifier 30 causes the transistor 18 to supply more current, which will cause the resistance of the gas sensor 14 to decrease until the two voltages provided to the control amplifier 30 are again equal.

In view of the foregoing description, it should be noted that the resistance of the gas sensor 14 stays substantially constant at all times, and that the voltage across the gas sensor 14 varies depending upon the particular type of gas present and its concentration.

A temperature sensor 40 (which may be an NTC thermistor) is disposed in the gas compartment 12 and is exposed to the gas therein. The temperature sensor 40 is connected in parallel to a resistor 42 and in series with a resistor 44. The resistors 42, 44 are connected between a relatively high reference voltage $V_H$ (e.g. 4.0 volts) and a relatively low reference voltage $V_L$ (e.g. 1.0 volts).

The resistance of the temperature sensor 40 changes in response to changes in temperature in the gas compartment 12, and thus the voltage at the junction of the temperature sensor 40 and the resistors 42, 44 changes in response to temperature. The voltage at that junction comprises a temperature signal which is related to the temperature in the gas compartment 12.

The magnitude of the electrical current flowing through the temperature sensor 40 depends on the magnitude of the voltages $V_L$ and $V_H$, the resistance values of the resistors 42, 44, and the resistance value of the temperature sensor 40. The resistance value of the resistor 44 is much larger (e.g. more than 100 times larger) than the resistance value of the resistor 16. Consequently, the current flow through the temperature sensor 40 is much less than the current flow through the gas sensor 14. As a result, since only a relatively small electrical current flows through temperature sensor 40, the resistance of the temperature sensor 40 does not significantly vary due to the heat capacity of the gas in the gas compartment 12, but depends only on the temperature of the gas in the gas compartment 12. Thus, the magnitude of electrical current flowing through temperature sensor 40 is substantially independent of, and different from, the magnitude of the current flowing through the gas sensor 14.

The temperature signal noted above is provided to the positive input of a difference amplifier 46 via a line 48. The negative input of the difference amplifier 46 is connected to receive an adjustable voltage via a line 50 connected to the output of an unity-gain operational amplifier 52 that acts as a buffer. The voltage output by the amplifier 52 is determined by the voltage provided to its positive input, which is generated from a resistive divider network composed of a resistor 54, a potentiometer 56 and a resistor 58. The potentiometer 56 is used to adjust the magnitude of the voltage provided on the line 50 to the difference amplifier 46 so that the output of the amplifier 46 can be adjusted or calibrated for a particular temperature.

The amplifier 46 generates a temperature signal which is transmitted to an operational amplifier 60 that is used as a level shift circuit. The amplifier 60 is optional and allows the magnitude of the temperature signal to be adjusted based on the magnitude of a level shift voltage provided to an input of the amplifier 60 via a line 62.

The amplifier 60 generates a temperature signal on a line 64 which is transmitted to the negative input of each of three difference amplifiers 70, 72, 74. The positive input of each of the difference amplifiers 70, 72, 74 is connected to receive the gas signal, described above, via a line 76 connected to the junction of the resistor 16 and the gas sensor 14.

The difference amplifier 70 has a relatively low gain (e.g. unity gain), which is determined by the ratio of the resistance of a resistor 78 to that of a resistor 80; the difference amplifier 72 has an intermediate gain (e.g. five), which is determined by the resistance values of a pair of resistors 82, 84; and the difference amplifier 74 has a relatively high gain (e.g. fifteen), which is determined by the resistance values of a pair of resistors 86, 88. Each of the difference amplifiers 70, 72, 74 generates a gas concentration signal at its output which has a magnitude equal to the difference between the magnitude of the gas signal on the line 76 and the magnitude of the temperature signal on the line 64, that difference being multiplied by the gain of the particular amplifier 70, 72, 74.

The use of three difference amplifiers 70, 72, 74, which allows the gas sensing apparatus 10 to have three different sensitivies to the presence of a gas, is not necessary, and only one of the difference amplifiers 70, 72, 74 could be used.

Prior to operation, the potentiometer 56 is adjusted so that the output of the amplifier 46 has a zero value for a reference temperature, e.g. 72° F. In operation, the voltage at the junction between the resistor 16 and the gas sensor 14 will change, depending on the heat capacity and concentration of the gas being sensed in the gas compartment 12, and the resultant gas signal will be transmitted to the amplifiers 70, 72, 74 via the line 76.

Any variance in temperature from the reference temperature noted above will cause the resistance of the temperature sensor 40 to change, causing the magnitude of the temperature signal on the line 64 to change. Specifically, an increase in temperature will cause a decrease in the magnitude of the temperature signal generated on the line 64, which will cause the magnitude of the gas concentration signals output by the difference amplifiers 70, 72, 74 to increase (since the temperature signal on the line 64 is subtracted from the gas signal on the line 76). Similarly, a decrease in temperature will cause the magnitude of the gas concentration signals output by the difference amplifiers 70, 72, 74 to decrease in magnitude.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A thermal gas sensing apparatus, comprising:

a gas compartment having an internal temperature and containing a gas having a heat capacity and a concentration;

a gas sensor exposed to said gas in said gas compartment and having a variable resistance;

a circuit portion coupled to said gas sensor adapted to generate a gas signal having a magnitude which relates to said heat capacity of said gas in said gas compartment;

a circuit portion adapted to supply a variable magnitude of electrical current through said gas sensor to cause said resistance of said gas sensor to remain substantially constant;

a temperature sensor exposed to said gas in said gas compartment;

a circuit portion coupled to said temperature sensor adapted to generate a temperature signal having a magnitude which relates to said temperature of said gas compartment;

a circuit portion for causing an electrical current to flow through said temperature sensor, said electrical current flowing through said temperature sensor having a magnitude which is substantially independent of said magnitude of said electrical current flowing through said gas sensor; and a circuit portion adapted to generate a gas concentration signal based upon said temperature signal and said gas signal, said gas concentration signal having a magnitude which relates to said concentration of said gas contained in said gas compartment.

2. An apparatus as defined in claim 1 wherein said circuit portion adapted to determine the difference between said adjustable voltage and said voltage across said temperature sensor comprises a difference amplifier.

3. An apparatus as defined in claim 1 wherein said circuit portion adapted to cause said electrical current to flow through said temperature sensor comprises a voltage source.

4. An apparatus as defined in claim 1 wherein said circuit portion adapted to generate said gas concentration signal comprises a difference circuit which determines the difference between said gas signal and said temperature signal.

5. An apparatus as defined in claim 4 wherein said difference circuit comprises a difference amplifier.

6. An apparatus as defined in claim 1 wherein said temperature sensor has a voltage thereacross and wherein said circuit portion adapted to generate said temperature signal comprises:

a circuit portion adapted to generate an adjustable voltage; and a circuit portion adapted to determine the difference between said adjustable voltage and said voltage across said temperature sensor.

7. An apparatus as defined in claim 6 wherein said circuit portion adapted to generate said adjustable voltage comprises a potentiometer.

8. An apparatus as defined in claim 1 wherein said circuit portion adapted to supply said variable magnitude of electrical current through said gas sensor comprises:

a current source which generates said electrical current; and a control circuit adapted to control said magnitude of said electrical current generated by said current source based upon said resistance of said gas sensor.

9. An apparatus as defined in claim 8 wherein said control circuit comprises an amplifier having a first input connected to sense a voltage across said gas sensor, a second input connected to sense a voltage across a fixed resistance, and an output connected to control said current source.

10. An apparatus as defined in claim 8 wherein said current source comprises a transistor.

11. A thermal gas sensing apparatus, comprising:

a gas compartment having an internal temperature and containing a gas having a heat capacity and a concentration;

a gas sensor exposed to said gas in said gas compartment and having a variable resistance;

a circuit portion coupled to said gas sensor adapted to generate a gas signal having a magnitude which relates to said heat capacity of said gas in said gas compartment;

a circuit portion adapted to supply a variable magnitude of electrical current through said gas sensor to cause said resistance of said gas sensor to remain substantially constant;

a temperature sensor exposed to said gas in said gas compartment;

a circuit portion coupled to said temperature sensor adapted to generate a temperature signal having a magnitude which relates to said temperature of said gas compartment; and circuit portion adapted to generate a gas concentration signal based upon the difference between said temperature signal and said gas signal.

12. An apparatus as defined in claim 11 wherein said circuit portion adapted to generate said gas concentration signal comprises a difference circuit adapted to determine the difference between said gas signal and said temperature signal.

13. An apparatus as defined in claim 11 wherein said circuit portion adapted to supply said variable magnitude of electrical current through said gas sensor comprises:

a current source which generates said electrical current; and a control circuit adapted to control said magnitude of said electrical current generated by said current source based upon said resistance of said gas sensor.

14. An apparatus as defined in claim 13 wherein said control circuit comprises an amplifier having a first input connected to sense a voltage across said gas sensor, a second input connected to sense a voltage across a fixed resistance, and an output connected to control said current source.

15. An apparatus as defined in claim 11 wherein said temperature sensor has a voltage thereacross and wherein said circuit portion adapted to generate said temperature signal comprises:

a circuit portion adapted to generate an adjustable voltage; and a difference circuit adapted to determine the difference between said adjustable voltage and said voltage across said temperature sensor.

16. An apparatus as defined in claim 15 wherein said circuit portion adapted to generate said adjustable voltage comprises a potentiometer.

17. A thermal gas sensing apparatus, comprising:

a gas compartment having an internal temperature and containing a gas having a heat capacity and a concentration;

gas sensor exposed to said gas in said gas compartment and having a variable resistance;

means coupled to said gas sensor for generating a gas signal having a magnitude which relates to said heat capacity of said gas in said gas compartment;

a circuit portion adapted to supply a variable magnitude of electrical current through said gas sensor to cause said resistance of said gas sensor to remain substantially constant, said circuit portion adapted to supply said variable magnitude of electrical current comprising:

a current source which generates said electrical current; and a control circuit adapted to control said magnitude of said electrical current generated by said current source based upon said resistance of said gas sensor, said control circuit comprising an amplifier having a first input connected to sense a voltage across said gas sensor, a second input connected to sense a voltage across a fixed resistance, and an output connected to control said current source;

a temperature sensor exposed to said gas in said gas compartment and having a voltage thereacross;

a circuit portion coupled to said temperature sensor adapted to generate a temperature signal having a magnitude which relates to said temperature of said gas compartment, said circuit portion adapted to generate said temperature signal comprising:

a circuit portion adapted to generate an adjustable voltage; and a difference circuit adapted to determine the difference between said adjustable voltage and said voltage across said temperature sensor;

a circuit portion adapted to cause an electrical current to flow through said temperature sensor, said electrical current flowing through said temperature sensor having a magnitude which is substantially independent of said magnitude of said electrical current flowing through said gas sensor; and a circuit portion adapted to generate a gas concentration signal based upon said temperature signal and said gas signal, said gas concentration signal having a magnitude which relates to said concentration of said gas contained in said gas compartment, said circuit portion adapted to generate a gas concentration signal comprising a difference amplifier for determining the difference between said gas signal and said temperature signal.

\* \* \* \* \*